US008568414B2

(12) United States Patent
Siravo et al.

(10) Patent No.: US 8,568,414 B2
(45) Date of Patent: *Oct. 29, 2013

(54) INTRAMEDULLARY ROD WITH SPIRALING FLUTES

(75) Inventors: Mark Siravo, Norristown, PA (US); Christoph Andreas Roth, West Chester, PA (US)

(73) Assignee: Depuy Synthes Products, LLC, Raynham, MA (US)

( * ) Notice: Subject to any disclaimer, the term of this patent is extended or adjusted under 35 U.S.C. 154(b) by 268 days.

This patent is subject to a terminal disclaimer.

(21) Appl. No.: 12/827,480

(22) Filed: Jun. 30, 2010

(65) Prior Publication Data
US 2010/0268229 A1    Oct. 21, 2010

Related U.S. Application Data

(63) Continuation of application No. 10/866,597, filed on Jun. 11, 2004, now Pat. No. 7,771,428.

(51) Int. Cl.
*A61B 17/58* (2006.01)
*A61F 2/30* (2006.01)

(52) U.S. Cl.
USPC ........................................................... 606/64

(58) Field of Classification Search
USPC .................. 606/62, 64, 67; 623/23.23, 23.27, 623/23.29, 23.35, 22.11, 23.15, 23.18, 623/23.26, 23.31
See application file for complete search history.

(56) References Cited

U.S. PATENT DOCUMENTS 3,709,218 A * 1/1973 Halloran ......................... 606/64
4,169,470 A * 10/1979 Ender et al. .................... 606/62
5,066,296 A * 11/1991 Chapman et al. .............. 606/64

* cited by examiner

*Primary Examiner* — Anu Ramana
(74) *Attorney, Agent, or Firm* — Fay Kaplun & Marcin, LLP

(57) ABSTRACT

An intramedullary rod for use in the treatment of long bone fractures includes an elongated rod extending along a longitudinal axis and including a head and a stem, at least a first transverse hole extending through the rod and a plurality of external spiral flutes located along at least a portion of the stem, wherein the elongated rod includes at least two bends along the longitudinal axis in a first plane and at least one bend along the longitudinal axis in a second plane.

20 Claims, 4 Drawing Sheets

INTRAMEDULLARY ROD WITH SPIRALING FLUTES

PRIORITY CLAIM

The present application is a Continuation application of U.S. patent application Ser. No. 10/866,597 filed on Jun. 11, 2004, now U.S. Pat. No. 7,771,428. The disclosure of the above patent is incorporated herein by reference.

FIELD OF THE INVENTION

This invention relates generally to systems for the internal fixation of bone fractures, and particularly, to intramedullary fracture fixation devices such as those used in, for example, the treatment of long bone fractures.

BACKGROUND OF THE INVENTION

Fractures of the long bones, such as the femur, are often treated with the use of an intramedullary rod ("IM rod") inserted into the medullary canal of the affected bone. An IM rod, as is well known in the art, generally comprises an elongated rod along with associated cross-members, such as screws or nails, including nailing devices with helical blades. The IM rod typically includes various transverse holes to allow for the placement of these associated cross-members through the IM rod and into bone tissue in order to stabilize and hold together the fragmented bone segments. For instance, in the treatment of fractures in the area of the neck and/or head of the femur, a cross-member can be inserted through the proximal portion of the IM rod, across the fracture, and then into the femoral head. For more distal shaft type fractures, locking screws can be placed through the IM rod and into bone tissue at appropriate locations to provide fixation of the bone fragments.

A technique for implanting intramedullary rods involves insertion of the rod through a point that is lateral to the center-line of the medullary canal, i.e. offset from the piriformis fossa. One of the many examples of the use of this technique is illustrated in U.S. Pat. No. 3,433,220 to Zickel. An osteotomy at the tip of the trochanter is made to create an entry site and a flexible reamer is utilized to carry out the reaming of the medullary canal while conforming to its basic anatomy. Because the location of the entry site is laterally offset from the axis of the medullary canal, an angled or curved opening is created between the entry site and the medullary canal.

Once the opening is made, an IM rod can be inserted through the entry site and into the medullary canal. However, the insertion point of an IM rod in a laterally offset placement is the site of possible iatrogenic fractures because the curvature of the opening into the medullary canal "angles" the rod into the medullary canal of the femur. This causes the potential for fracture due to the inadvertent application of transverse point loads against the bone. Fractures have been observed beginning at the entry site and extending through the intertrochanteric region following IM rod insertion.

In addition, the shape of the medullary canal of the femur itself can complicate the insertion of an IM rod. The medullary canal has a gentle, uniform, anterior bowing throughout its length. If the IM rod does not possess an anterior bend or curvature, transverse point loads may act against the cortical wall of the femur leading to fracture. Over-reaming of the medullary canal can prevent fracturing of the shaft during insertion, but this results in a decrease of the surface area contact between the rod and the bone, leading to less effective fixation of the bone fragments. Another detrimental effect of over-reaming is a decrease in the bending and torsional strength of the bone. As a result, many IM rods have anterior bends or curves in the anterior-posterior plane to match the normal medullary anatomy of the femur, as exemplified in the prior art by patents such as U.S. Pat. No. 3,433,220 to Zickel and U.S. Pat. No. 4,135,507 to Harris.

However, curvature of the rod in the anterior-posterior plane alone does not necessarily overcome the difficulties arising from the insertion of the IM rod through the laterally offset entry site. Additional side point loads may be imposed on the bone by the proximal segment of the IM rod once the rod is in its final position because the anterior curvature of the rod is in an orthogonal plane to the curvature of the opening between the entry site and the medullary canal. This may also result in subsequent fracturing of the femur. As a result, some IM rods (such as disclosed in the prior art Zickel and Harris patents) have incorporated a bend or curve in the lateral-medial plane that attempts to conform with the opening from the entry point into the medullary canal. Nevertheless, these laterally curved rods have not been completely successful in eliminating inadvertent fracturing during the insertion or removal procedure.

When an IM rod is provided with an anterior curve, rotating the rod approximately 90 degrees about its longitudinal axis prior to insertion may facilitate its insertion into the medullary canal because the rod's curvature could more closely approximate the curvature of the opening between the entry site and the medullary canal. Thus, the rod is initially inserted in this rotated orientation and then twisted as it is driven into the medullary canal to its final position. However, applying the proper amount of twisting force at the appropriate time is problematic as it may be difficult to continuously monitor the precise extent of the rod's progress into the medullary canal while also applying the corresponding amount of twist required at each point. In addition, IM rods are often provided with external flutes extending straight down the surface of the shaft of the rod that may interfere with this twisting motion during insertion. While these external flutes are desirable because they provide benefits such as improved medullary revascularization, reduced stiffness with greater strength, and improved torsional fixation at the rod-bone interface, the engagement of the flutes with bone inside the medullary canal may actually impede the twisting necessary in order to insert the rod.

SUMMARY OF THE INVENTION

The IM rod of the present invention preferably provides a rod with multiple curved sections in different planes designed to conform with the curvature or bend of the long bone in which it is inserted, both during insertion and in the rod's final position in the long bone. In addition, the multiple curved sections in different planes may overlap resulting in a co-planar curvature of portions of the IM rod which assist in the insertion process by guiding the proper rotation of the IM rod as it is inserted into the bone. Spiraling flutes extending down the distal portion of the rod also assist in properly guiding and orienting the rod about its longitudinal axis during insertion such that the appropriate segment of the curved rod conforms with the appropriate portion of the bone at the appropriate location.

The IM rod comprises an elongated rod with a proximal head, a distal stem and transverse holes preferably provided at a variety of locations along its length to accept cross-members, thus allowing effective fixation of a number of different types of fractures. The rod additionally may comprise at least two non-tangential (i.e. not touching) curved sections in the lateral-medial plane, and preferably at least a third curve in the anterior-posterior plane. The stem may include flutes that extend down the surface of the rod and preferably twist approximately 90 degrees about the longitudinal axis of the rod. Various cross-members such as, for example, screws, bolts, nails, and/or tacks may be provided for insertion through the transverse holes and into bone tissue.

Prior to insertion into the femur, the rod is rotated about its longitudinal axis such that the anterior curvature of the rod will roughly conform to the lateral curvature of the opening between the entry site and the medullary canal. As the surgeon pushes the rod into the opening, progressive rotation of the rod about its longitudinal axis at the appropriate time, e.g. when the rod is inserted an appropriate distance into the entry site, is guided preferably both by the spiral flutes and the curved portions of the IM rod. This rotation allows the anterior curvature of the rod to conform with the curvature of the long bone with a minimum of transverse point loading from the rod due to the insertion procedure. If the curved portions of the rod were improperly placed due to incorrect rotation of the rod, the curved sections could potentially apply loads against the side of the bone leading to secondary fractures of the bone. Finally, as insertion nears completion, the curved segments of the rod located closer to the proximal end of the rod are rotated into their proper position within the bone and ultimately align themselves within the bone opening.

As a result of the features of the preferred IM rod, the potential for iatrogenic fracturing of the long bone, such as for example the femur, is decreased because the surgeon is assisted in inserting a properly shaped rod into the long bone (without applying adverse forces to the bone), with a precision that would be difficult to achieve with prior art IM rods. It is envisioned that these features, singularly or in combination, could also be adapted to any of the long bones (i.e. humerus, radius/ulna, femur, tibia/fibula) and to other types of internal fracture fixation devices to likewise ease their use.

BRIEF DESCRIPTION OF THE DRAWINGS

The disclosed figures are for purposes of description and may illustrate preferred features of the IM rod which may be optional, and which further may be combined or used singularly. These figures are intended to be illustrative only and in no way serve to limit the scope of the invention. The present invention is limited only by the claims.

DETAILED DESCRIPTION OF THE INVENTION

Figure 1:
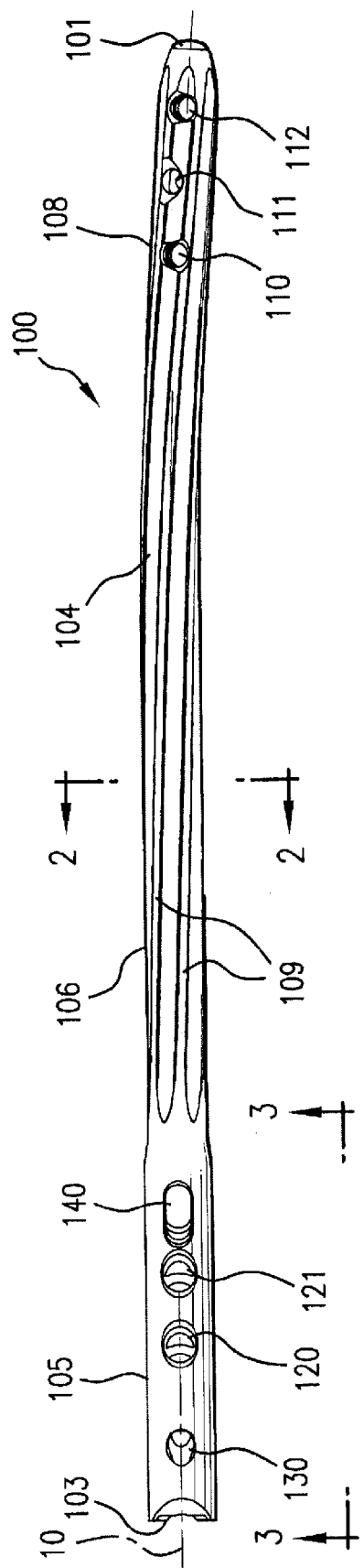
FIG. 1 is a profile view of a preferred embodiment of the intramedullary rod with spiraling flutes.
Figure 2:
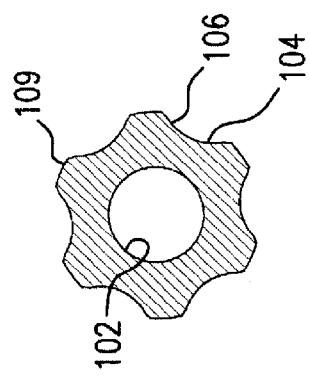
FIG. 2 is a cross-sectional view of the intramedullary rod, through line 2-2 of FIG. 1.

FIGS. 1 and 2 show the preferred embodiment of the IM rod of the present invention which is designed for insertion into and for the treatment of the femur. Although the IM rod will be described for use in the femur, it will be appreciated that its features have application in IM rods for long bones including the humerus, radius/ulna, femur, tibia/fibula, or even other bones. The IM rod of the present invention is designed for the treatment of a variety of fractures and preferably comprises a central bore 102 extending the length of the intramedullary rod 100 with an opening 103 to the exterior at the head portion 105 and an opening 101 to the exterior at the stem 108, creating a cannulated rod. The cannulation allows the rod to be placed over a guide wire inserted into the bone for guidance and alignment. Likewise, the cannulation of the rod may be omitted if desired or appropriate, such as with a smaller diameter or shorter length IM rod. The rod may be provided in varying lengths and diameters to allow the surgeon to properly match the final dimensions of the rod with the physical and medical characteristics of the patient being treated. The rod is preferably composed of a biologically non-reactive metal such as titanium or a metal alloy such as a titanium alloy, other metals such as stainless steel or non-metal materials, although other materials could conceivably be used as well.

Figure 3:
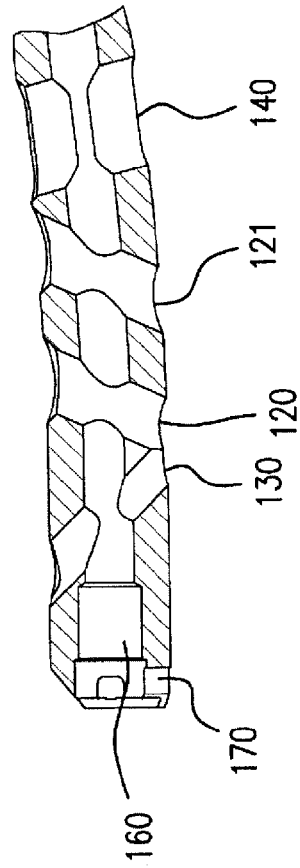
FIG. 3 is a cross-sectional view of a portion of the intramedullary rod, through line 3-3 of FIG. 1, showing the various openings provided at the head of the rod.

Preferably, the rod 100 may include transverse openings located in the lateral-medial plane of the IM rod as shown in FIG. 3. The head portion 105 optionally may include transverse holes 120 and 121, a transverse hole 130, and/or an elongated transverse hole 140. Each of these openings may have an axis which extends through the IM rod at an angle which produces fracture fixation characteristics desired by the surgeon. For example, transverse holes 120 and 121 are preferably oriented at an angle of between 35° and 75° from the longitudinal axis of the rod, and most preferably at an angle of 66°. Transverse holes 120 and 121 may have parallel axes and may have equal diameter bores. Transverse hole 130 is preferably oriented at an angle of 25° and 75° from the longitudinal axis of the rod, and most preferably at an angle of 45°. Elongated transverse hole 140 is preferably oriented at an angle of between 5° and 35° from the longitudinal axis of the rod, and most preferably at an angle of 16°. These transverse openings are sized to accept cross-members such as, for example, screws or nails which engage the bone tissue of the affected bone. For example, if a femoral neck fracture is being treated, one or more femoral neck screws 200, shown in FIG. 4, can be inserted through transverse holes 120 and 121, and then into the head of the femur. Preferably, the femoral neck screws utilized are 6.5 mm diameter titanium lag screws. Different size transverse holes 120, 121 may be provided to accommodate different size cross-members. The first neck screw may also be a different size than the second neck screw. The threaded ends 210 of the femoral neck screws may engage and secure the femoral head, while the optional use of two of these screws prevents rotation of the femoral head relative to the femur. It is envisioned that other appropriate fixation cross-members known in the art such as nails, helical blades, tacks, bolts, pins or the like could also be utilized for securing the femoral head, as they could be for any of the other fixation situations described herein.

In the treatment of femoral shaft fractures, locking screws can be inserted through transverse hole 130 and/or elongated hole 140, and then into the lesser trochanter to provide stable fixation in both the longitudinal direction and torsionally. The optional use of a single locking screw through elongated hole 140 allows the proximal portion of the femur to move in relation to the distal end of the rod, thereby providing torsional fixation alone. Other fixation or anchoring members such as nails (including those with helical blades), tacks, bolts, pins, etc. may be inserted through holes 130, 140.

The stem 108 of the rod preferably includes distal transverse holes 110, 111 and 112. Distal holes 110 and 112 may be located in the lateral-medial plane of the IM rod. Distal hole 111 preferably is angularly offset by 25° about the longitudinal axis of the rod from distal holes 110 and 112. Locking screws can be inserted through the bone into distal hole 111, and into either or both distal holes 110, 112 to lock the distal portion of the rod to the femur. By inserting the locking screws in different planes, the rod can be secured to the bone with greater stability. Other fixation or anchoring means such as nails (including those with helical blades), tacks, bolts, pins, etc. may be inserted through holes 110, 111, 112.

The stem 108 of the rod includes channel-like formations 104 with "flutes" 109 formed in between the channels 104 along the surface 106 of the stem 108. The flutes preferably extend from below the base of the head portion 105 down to the distal end of the stem 108. Most preferably, the flutes 109 begin about 75 mm to 95 mm from the proximal end of the rod. Like flutes known in the art, flutes 109 provide benefits such as improved medullary revascularization, reduced stiffness with greater strength, and improved torsional fixation at the rod-bone interface. In a preferred embodiment, as shown in FIG. 2, there are six flutes 109 although more or less may be implemented. Flutes 109 preferably do not extend down the stem of the rod in a straight path parallel to the longitudinal axis 10 of the rod, but rather extend in a spiral or helical fashion down the length of the stem 108 as can be seen in FIG. 1. The flutes preferably rotate or twist through approximately 90 degrees about the longitudinal axis 10 of the IM rod as they travel from their start point to their termination point. However, the amount of rotation may vary as desired. The direction of the rotation generally depends upon whether the IM rod is being inserted into the left side or the right side of the body because the IM rod is preferably rotated to the rear of the patient. When viewing the rod from its proximal end to its distal end, the flutes will rotate counter-clockwise on the left side rods and clockwise on the right side rods. Understandably, the direction of rotation could vary depending on the use and structure of the IM rod.

The flutes 109 are preferably formed by milling the surface of the stem to form the spiraling flutes of the rod 100. However, the flutes 109 could also be formed by other means known to those of skill in the art. In addition, other types of surface deformations or protrusions could conceivably fulfill the role of flutes 109.

As the rod 100 is inserted through the entry site, preferably located at the greater trochanter, offset from the piriformis fossa of the femur, and into the femoral canal, the flutes 109 tend to engage bone tissue and therefore guide the twisting motion of the rod. Unlike an IM rod with straight flutes, which would impede the rotation of the rod during insertion, the spiral flutes 109 of the rod 100 actually assist in twisting the rod. Because the rate of rotation of the spiral about the longitudinal axis is predetermined, the proper amount of rotation is applied to the rod 100 as a function of the extent of insertion. This greatly facilitates the proper insertion and final alignment of the curved rod, and reduces the potential for inadvertent bone fracturing due to either premature or delayed twisting of the rod 100. Also, bone tissue is spared from the cutting that would occur from twisting an IM rod with straight flutes.

Removal of the rod from the femur is also facilitated by the presence of the spiral flutes 109. During the healing process, bone ingrowth may cause the IM rod 100 to be tightly embedded within the medullary canal. The spiral flutes 109 facilitate removal by guiding the rotation of the rod 100 as it is pulled from the medullary canal, applying the appropriate amount of twist to the rod so that the curved sections will apply reduced transverse pressure to the bone as the rod 100 is removed.

Figure 6:
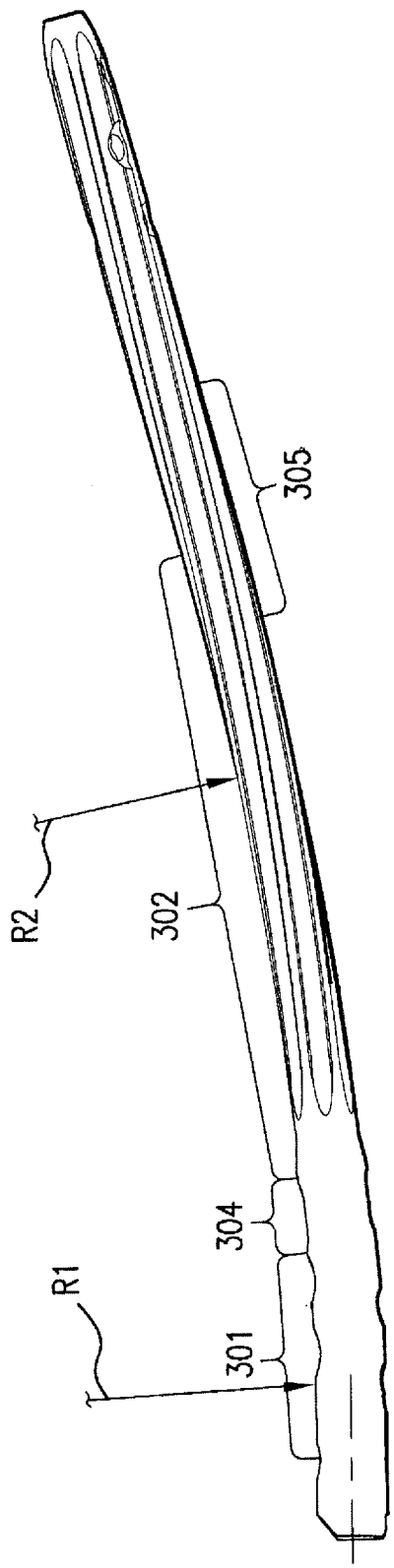
FIG. 6 is a profile view of the intramedullary rod with spiraling flutes of the present invention, showing the curvatures located in the lateral-medial plane of the device.
Figure 7:
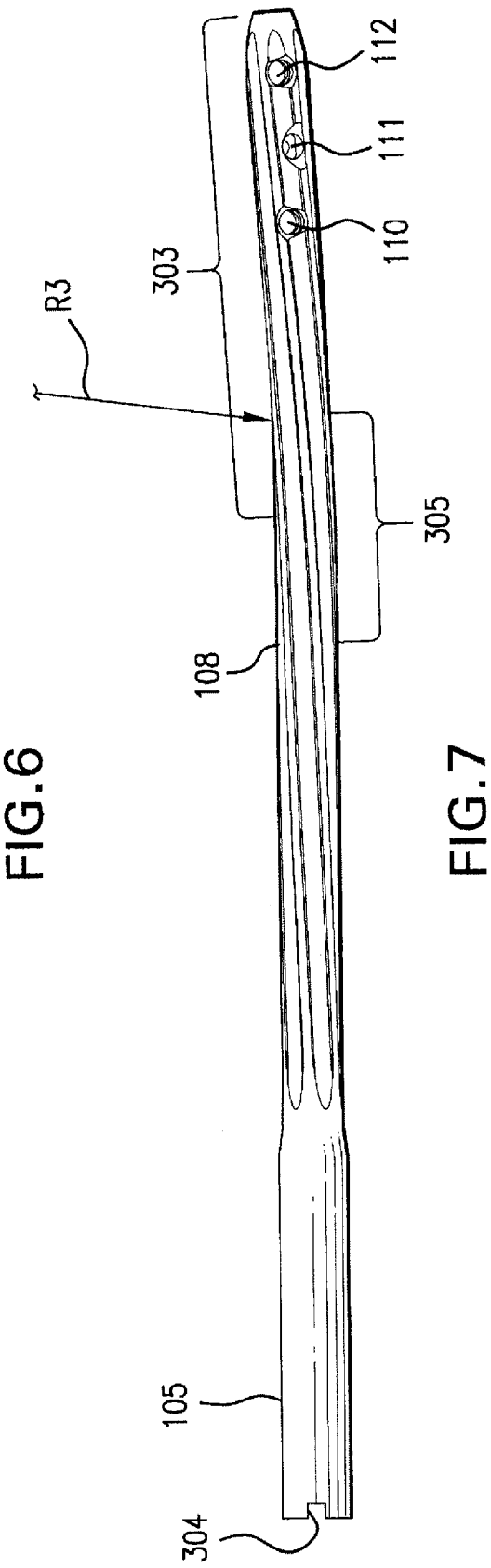
FIG. 7 is a profile view of the intramedullary rod with spiraling flutes of the present invention, showing the curvatures located in the anterior-posterior plane of the device.

The rod 100 preferably has three curved sections 301, 302, 303 along its length, preferably with two of the curves located in the same plane and the third preferably located in an orthogonal plane, as shown in FIGS. 6 and 7. The various curves in the rod are formed using a commercially available, computer controlled, bending machine capable of incorporating these complex curvatures into the rod 100. Other methods of creating these curved sections are known and may also be utilized in the construction of the device.

Figures 4, 5:
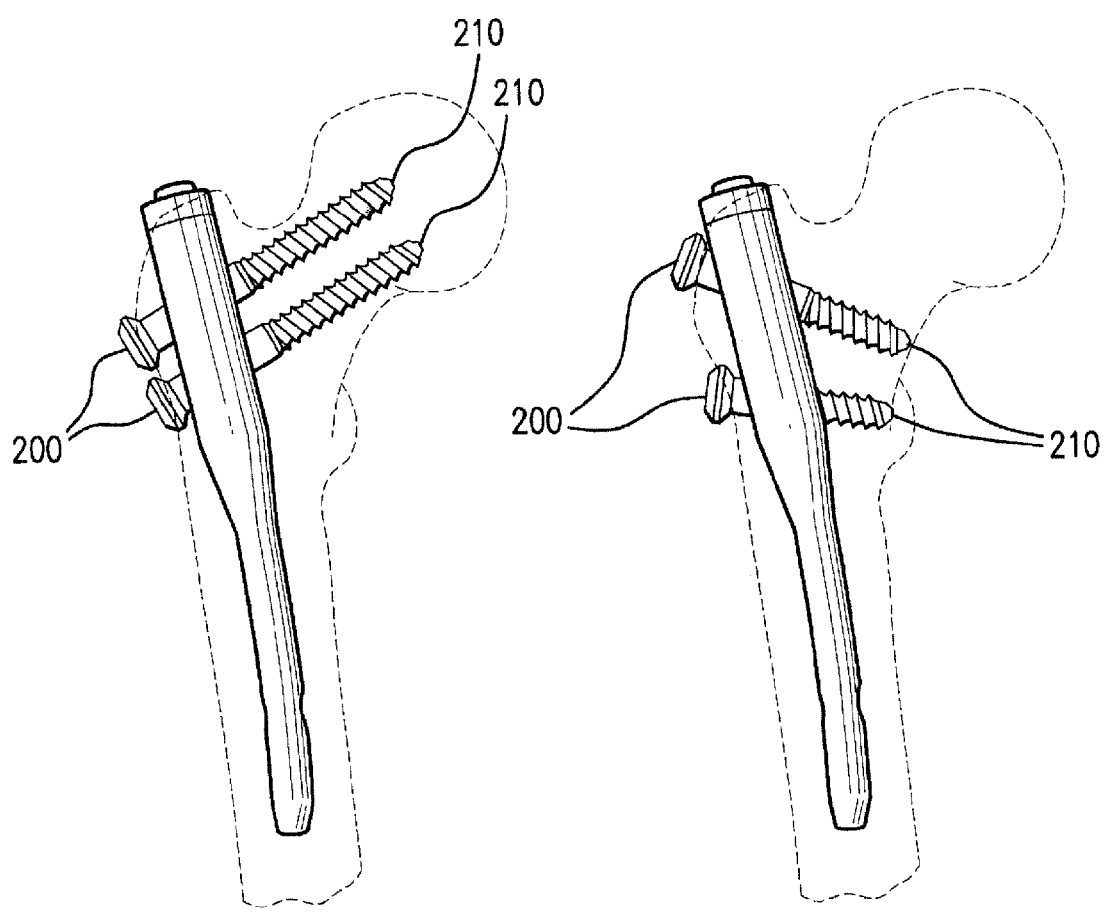
FIG. 4 illustrates the intramedullary rod of the present invention inserted into a femur, with two cross-members extending through the rod and into the femoral head.
FIG. 5 illustrates the intramedullary rod of the present invention inserted into a femur, with two cross-members extending from the greater trochanter to the lesser trochanter.

The first curved segment 301 preferably begins at the proximal head 105 and preferably ends at a straight segment 304. Most preferably, the first curve 301 begins about 26 mm from the proximal end of the IM rod and is bent to about a 6.5° arc angle. The first curve 301 preferably has a radius of curvature R1 of between about 100 mm and about 500 mm and more preferably about 300 mm (approx. 11.8 inches). The first curve may start at a different location, be bent to a different angle and may have a different radius of curvature. In addition, the radius of curvature R1 for the first curve 301 may vary over the length of the first curved segment. The first curved segment may have a length in one embodiment from about 10 mm to about 60 mm and more preferably may be about 34 mm for an IM rod intended to be inserted in the femur. The length of first curved segment 301 may be longer or shorter than the values recited above depending upon the design needs. When the rod 100 is placed into its final position within the femur, the first curve 301 lies in the lateral-medial plane of the femur and is directed transversely away from the body, towards the entry site at the tip of the trochanter, as illustrated in FIGS. 4 and 5.

The second curved segment 302 lies in the same plane as the first curve 301, but begins at a point beyond the termination of the first curve, preferably below the head 105 of the rod 100. Most preferably, the second curved segment 302 begins about 75 mm from the proximal end of the IM rod and is bent to about an 8.5 degree arc angle. A straight segment 304 of the IM rod preferably separates first curved segment 301 and second curved segment 302 from each other. The second curved segment 302 preferably has a radius of curvature R2 of between about 100 mm and about 1500 mm, and more preferably about 800 mm (approx. 31.5 inches). The second curved segment 302 may start at a different location and may have a different radius of curvature. In addition, the radius of curvature R2 for the second curved segment 302 may vary or change over the length of the second curved segment 302. The second curved segment 302 may have a length in one embodiment from about 10 mm to about 220 mm, and more preferably may be about 120 mm in length for an IM rod intended to be inserted into the femur. The length of the second curved segment 302 may be more or less than the values recited above depending upon the design needs.

The nature of the first and second curved segments 301, 302 is such that the IM rod preferably more properly conforms with the transition of the cavity formed in the bone that extends from the insertion point and into the medullary canal than if the rod were merely straight. Accordingly, there is a reduction of unnecessary transverse loads acting on the bone from the intramedullary rod and this helps to reduce the risk of an inadvertent secondary fracture arising from the insertion or removal process.

As shown in FIG. 7, the third curved segment 303 preferably is between 70°-120°, and more preferably orthogonal to the first and second curved segments 301, 302 and is preferably located in the anterior-posterior plane to match the anterior curvature of the medullary canal. Preferably, the third curve 303 begins at a point along the stem 108 of the rod 100. Most preferably, the third curve 303 begins about 180 mm from the proximal end of the IM rod and continues to the end of the rod. The third curve preferably has a radius of curvature R3 of between about 500 mm and about 2500 mm, and more preferably about 1000 mm (approx. 39.4 inches). The third curve may start at a different location, or end at a different location, and may have a radius of curvature R3 that is different than the values recited above. In addition, the radius of curvature R3 for the third curved segment 303 may vary or change over the length of the third curved segment 303. The third curved segment 303 may have a length in one embodiment from about 10 mm to the remaining length of the IM rod. The length of the third curved segment 303 may be more or less than the values recited above depending upon the design needs.

The third curved segment 303 is formed in a manner that preferably conforms with the natural curvature of the bone and therefore helps to reduce the risk of an inadvertent secondary fracture. The third curved segment 303 also preferably partially overlaps the second curved segment 302 to form a co-planar curve that results in the rod 100 having a "twist" through this section. In other words the IM rod in this overlapping section 305 curves in two planes. Most preferably, the second curve 302 and the third curve 303 overlap each other by approximately 20 mm, however, the amount of overlap could vary within the range of approximately 0 mm to the length of the IM rod. As with the spiral flutes 109, this twist assists in guiding the rotation of the rod about its longitudinal axis as it is inserted into the medullary canal. The configuration of the twist results in the rotation of the rod in the same direction of rotation that the spiral flutes rotate the IM rod.

In use, the surgeon chooses an appropriately sized IM rod 100 based upon the patient's physical characteristics and medical condition. To assist in the insertion of both the IM rod 100 itself and the various cross-members into proximal transverse holes 120, 121, 130 and 140 of the rod, a guide tool (not shown) in the form of an insertion handle is mounted to a hole 160, preferably threaded, located at the top of the head portion 105 of the rod. A slot 170 is used to align the insertion handle with the IM rod 100 about the longitudinal axis of the rod 100. Thus, when the IM rod 100 is within the medullary canal of the bone, the orientation of the rod 100 can be identified by the position of the handle.

An osteotomy at the tip of the greater trochanter is made to create an entry site and a flexible reamer is used to create a cavity in the medullary canal. The surgeon then orients the IM rod 100 so that it is rotated 90 degrees about its longitudinal axis from its final position, thereby roughly orienting the anterior-posterior curvature of the rod with the curved opening from the entry site to the medullary canal. As the surgeon pushes the stem of the IM rod 100 into the medullary canal, the spiral flutes 109 and the co-planar curvature of the rod help to guide the rotation of the IM rod 100 approximately 90 degrees so that the various curves conform with the opening through the bone.

Once the rod 100 is fully inserted into position within the bone, an aiming arm on the insertion handle is used to locate the transverse holes through the rod 100. Cross-members are aligned with their respective holes through the rod 100 and inserted into the bone and through the rod to fix the bone as required by the type of fracture being treated.

Figure 8:
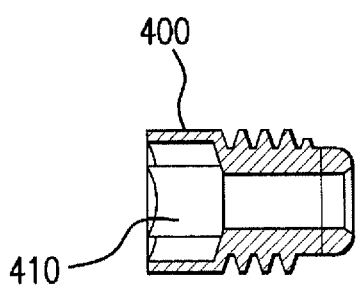
FIG. 8 is a cross-sectional view of an end cap.
Figure 9:
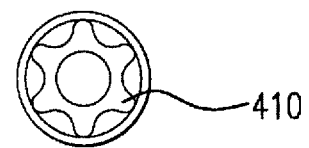
FIG. 9 is an end view of an end cap.
Figure 10:
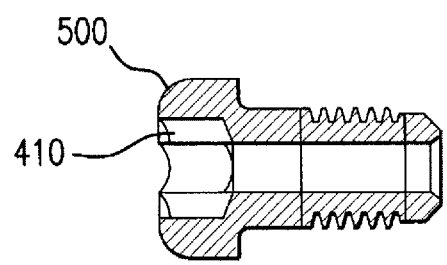
FIG. 10 is a cross-sectional view of an alternative end cap.

After insertion of the rod and cross-members, an end cap 400 (shown in FIG. 8) can be installed in the hole 160 to prevent bony ingrowth within the hole. End cap 400 is designed to be recessed within the head 105 of the rod 100 once installed, while an alternative end cap 500 (shown in FIG. 10) extends beyond the head 105 of the rod 100 to extend the rod's overall length as desired. Both end caps are provided with sockets 410 (shown in FIG. 9) for the insertion of an appropriate installation tool.

It will be appreciated that certain preferred embodiments and features of the IM rod have been described and illustrated, but numerous modifications and other embodiments may be devised by those skilled in the art. For example, although the IM rod has been described with reference to its use in the femur, the IM rod could be used in the treatment of other long bones using some or all of the features described herein with the size and shape optionally being changed. The features described herein may be used singularly or in combination. Therefore, it will be understood that the appended claims are intended to cover all such modifications and embodiments which come within the spirit and scope of the present invention and the invention will be defined by the claims given their broadest interpretation.

What is claimed:

1. An intramedullary rod for use in the treatment of long bone fractures, comprising:
   an elongated rod extending along a longitudinal axis and including a head and a stem;
   at least a first transverse hole extending through the rod; and
   a plurality of external spiral flutes located along at least a portion of the stem,
   wherein the elongated rod includes a first bent portion and a second bent portion, the first and second bent portions curving relative to the longitudinal axis in a first plane, and a third bent portion curving relative to the longitudinal axis in a second plane, and wherein the curvature of the third bent portion matches an anterior curvature of a medullary canal into which the rod is to be inserted.

2. The intramedullary rod of claim 1, wherein the first bent portion has a first radius of curvature and the second bent portion has a second radius of curvature, the first radius of curvature being different than the second radius of curvature.

3. The intramedullary rod of claim 2, wherein the third bent portion has a third radius of curvature, the third radius of curvature being different than the first radius of curvature.

4. The intramedullary rod of claim 3, wherein the third radius of curvature is larger than the first and second radii of curvature.

5. The intramedullary rod of claim 3, wherein the first radius of curvature is between 100 mm and 500 mm, the second radius of curvature is between 100 mm and 1500 mm, and the third radius of curvature is between 500 mm and 2500 mm.

6. The intramedullary rod of claim 2, wherein the second radius of curvature is larger than the first radius of curvature.

7. The intramedullary rod of claim 1, wherein the first bent portion is separated from the second bent portion by a substantially straight section.

8. The intramedullary rod of claim 1, wherein one of the first and second bent portions and the third bent portion overlap one another along the longitudinal axis of the elongated rod.

9. The intramedullary rod of claim 1, wherein the flutes are formed by spiral projections.

10. The intramedullary rod of claim 1, further comprising a plurality of spiral channels formed along at least a portion of the stem.

11. The intramedullary rod of claim 1, wherein the first and second bent portions each have a center of curvature, and both centers of curvature are located on the same side of the longitudinal axis in the first plane.

12. The intramedullary rod of claim 1, wherein the first bent portion extends for about 10 mm to about 60 mm.

13. The intramedullary rod of claim 1, wherein the second bent portion extends for about 10 mm to about 220 mm.

14. The intramedullary rod of claim 1, wherein an orientation of the flutes changes by about a 90 degree angular rotation with respect to the longitudinal axis of the rod.

15. The intramedullary rod of claim 1, wherein the at least first transverse hole comprises:
   a pair of holes located in the head having substantially parallel axes oriented at a first angle with respect to the longitudinal axis of the rod; and
   a bore located in the head, the bore having an axis oriented at a second angle with respect to the longitudinal axis of the rod.

16. The intramedullary rod of claim 15, further comprising an elongated hole located in the stem, the hole having an axis oriented at an angle with respect to the longitudinal axis of the rod.

17. The intramedullary rod of claim 16, wherein the angle of the elongated hole is substantially the same as the bore.

18. The intramedullary rod of claim 16, wherein the angle of the elongated hole is different than the angle of the bore.

19. An intramedullary rod for use in the treatment of long bone fractures, comprising:
   an elongated rod extending along a longitudinal axis and including a head and a stem, the head and stem each having a maximum outer diameter, where the maximum outer diameter of the head is greater than the maximum outer diameter of the stem;
   at least a first transverse hole extending through the head of the rod; and
   a plurality of external spiral flutes located along at least a portion of the stem,
   wherein the elongated rod includes a first bent portion and a second bent portion, the first and second bent portion curving relative to the longitudinal axis in a first plane, and a third bent portion curving relative to the longitudinal axis in a second plane, and wherein the curvature of the third bent portion matches an anterior curvature of a medullary canal into which the rod is to be inserted.

20. The intramedullary rod of claim 19, wherein each of the plurality of flutes has a start point and a termination point on the stem of the rod, and each flute rotates approximately 90 degrees about the longitudinal axis of the rod as it travels from its start point to its termination point.

* * * * *